United States Patent [19]

Hopkins

[11] Patent Number: 4,540,668

[45] Date of Patent: Sep. 10, 1985

[54] ALCOHOL OXIDASE FROM PICHIA-TYPE YEASTS

[75] Inventor: Thomas R. Hopkins, Bartlesville, Okla.

[73] Assignee: Phillips Petroleum Company, Bartlesville, Okla.

[21] Appl. No.: 258,177

[22] Filed: Apr. 27, 1981

Related U.S. Application Data

[63] Continuation of Ser. No. 45,715, Jun. 5, 1979, abandoned.

[51] Int. Cl.³ .......................... C12N 9/04; C12Q 1/26; C12R 1/84
[52] U.S. Cl. ...................................... 435/190; 435/25; 435/938; 435/816
[58] Field of Search .......................... 435/25, 190, 938

[56] References Cited

U.S. PATENT DOCUMENTS

| | | | |
|---|---|---|---|
| 2,926,122 | 2/1960 | Goldsmith | 195/66 |
| 3,005,714 | 10/1961 | Cooper | 99/54 |
| 3,265,587 | 8/1966 | Doebbeling et al. | 195/66 |
| 3,269,918 | 8/1966 | Barton | 195/66 |
| 3,701,715 | 10/1972 | Lakshminarayanan | 195/65 |
| 3,930,953 | 1/1976 | Stark | 195/62 |
| 4,071,407 | 1/1978 | Hall | 195/62 |
| 4,073,713 | 2/1978 | Newman | 435/817 X |
| 4,250,261 | 2/1981 | Eggeling et al. | 435/190 |

FOREIGN PATENT DOCUMENTS

| | | |
|---|---|---|
| 2830327 | 3/1980 | Fed. Rep. of Germany . |
| 1507810 | 4/1978 | United Kingdom . |
| 1508247 | 4/1978 | United Kingdom . |

OTHER PUBLICATIONS

Kato et al., Agr. Biol. Chem., vol. 38, No. 3, pp. 675–677, (1974).
Kato et al., Agr. Biol. Chem., vol. 38, No. 1, pp. 111–116, (1974).
Janssen et al., Biochim Biophy. Acta, 151, 330–342, (1968).
Guilbault et al., Analytical Letters, vol. 2, pp. 41–48, (1969).
Tani et al., Advances in Applied Microbiology, vol. 24, (1978), pp. 165–186.
Kato et al., Agr. Biol. Chem., vol. 36, pp. 2411–2419, (1972).
Chemical Abstracts, 92: 144972r, (Abstract of Ger. Offen. 2 830 327).
Couderc et al., Agr. Biol. Chem., 44(10), 2279–2289, Oct. 1980.
Baratti et al., Biotechnology and Bioengineering, vol. XX, pp. 333–348, (1978).
Yamada et al., Agr. Biol. Chem., 43(4), 877–878, (1979).
Chemical Abstracts, 89: 103375t, (1978).
Guilbault et al., Analytical Chimica Acta, vol. 69, pp. 189–194, (1974).
Janssen et al., Methods in Enzymology, vol. 41B, pp. 364–369, (1975).
Nanjo et al., Analytical Chimica Acta, vol. 75, pp. 169–180, (1975).
Kato et al., Eur. Journal Biochemistry, vol. 64, pp. 341–350, (1976).
Clark, Biotechnol. & Bioeng. Symp., No. 3, 377–394, (1972).
Fujii et al., Agr. Biol. Chem., vol. 36, pp. 2297–2306, (1972).
Tani et al., Agr. Biol. Chem., vol. 36, pp. 68–83, (1972).

*Primary Examiner*—Lionel M. Shapiro

[57] ABSTRACT

A new alcohol oxidase is isolated from Pichia-type microorganisms in soluble or crystalline form. The crystalline novel enzyme is isolated by preparing an aqueous fluid containing cells of a Pichia-type microorganism, homogenizing the fluid and separating solids therefrom to produce an alcohol oxidase solution, adjusting the solution to have an ionic strength in the range of 0.05 to 0.01 in ionic strength to form a recovery range solution thereby causing the crystalline alcohol oxidase to form. The new enzyme is used to determine alcohol concentrations in fluid samples in which conditions are compatible with the enzyme's activity.

16 Claims, No Drawings

ALCOHOL OXIDASE FROM PICHIA-TYPE YEASTS

This is a continuation of application Ser. No. 045,715 filed June 5, 1979 now abandoned.

FIELD OF THE INVENTION

The invention relates to a novel alcohol oxidase. In another aspect, the invention relates to a novel crystalline alcohol oxidase. In other aspects, the invention relates to methods for production and isolation of such novel alcohol oxidases.

BACKGROUND OF THE INVENTION

Alcohol oxidases are known to be produced by various microorganisms grown on methanol, though not on ethanol. These alcohol oxidases catalyze the reaction $$RCH_2OH + O_2 \rightleftharpoons RCHO + H_2O_2$$

where R is hydrogen or a lower alkyl, generally selected from the group H—, $CH_3$—, $CH_3CH_2$—, and $CH_3(CH_2)_2$—. Alcohol oxidases can be used to scavenge or remove oxygen from compatible solutions, as well as in the production of aldehydes and hydrogen peroxide. In combination with a suitable test probe, the alcohol oxidase enzme can be employed to determine alcohol concentration, especially the concentrations of such alcohols as methanol and ethanol. Hence, such enzymes are useful in applications such as the measurement of alcohol levels in biological fluids, for example blood, and the like.

Some uses of these enzymes have been hindered by unavailability of the pure enzyme in commercially reasonable quantities for proposed uses. One of the problems encountered with previous types of alcohol oxidase is that, in common with many enzymes, they are difficult to isolate in relatively pure form, for example in a form essentially lacking catalase activity. A variety of techniques, such as fractional precipitation using materials such as ammonium sulfate, alcohol or polyethylene glycol, or column chromatography using ion exchange resins or gel molecular sieve media, having been utilized to prepare the purified enzyme. Isolation of relatively pure alcohol oxidase by the use of such techniques is difficult, and material and time consuming, accounting for much of the cost of the commerical enzyme. The resulting high costs of relatively pure alcohol oxidases lead to restricted usage of these enzymes, and discourage potential use of the enzyme in applications requiring large quantities of the enzyme as well as discouraging the search for new applications. Moreover, as is known in the art, stability of the known prior alcohol oxiadase enzymes to temperature and pH, the specificity for particular substrates, and susceptibility to inhibition by these compounds and others, as well as the rate of the catalyzed reaction also affect the potential uses to which such enzymes are most efficiently and effectively placed.

SUMMARY OF THE INVENTION

I have discovered a novel alcohol oxidase exhibiting properties differing from known alcohol oxidases in some of its properties and particularly in its unusual character in ease of crystallizing in recovery operations such as dialysis. The novel alcohol oxidase is obtained from methanol-utilizing Pichia-type microorganisms comprising microorganisms of genus Pichia and microorganisms genetically and/or taxonomically closely related to Pichia.

In accordance with one aspect of my invention a novel alcohol oxidase is prepared. In another aspect, a novel crystalline alcohol oxidase is prepared. In yet other aspects, methods are provided to prepare such novel enzymes. In a further aspect, novel uses of the alcohol oxidases are provided.

In accordance with one aspect of my invention, my method comprises preparing an aqueous fluid suspension of cells of a methanol-utilizing Pichia-type microorganism. The aqueous fluid containing a suspension of cells is homogenized to produce a homogenate. Suspended solids are removed from the homogenate to produce a crude solution having useful enzymatic activity containing the novel alcohol oxidase as a soluble alcohol oxidase. My method further comprises preparation of the novel alcohol oxidase in crystalline form, particularly desirable for commercial usages. The crystalline form can be obtained by methods of ultra filtration, presently preferably and conveniently by dialysis; or by other separation methods. Dialysis comprises dialyzing the crude solution, prepared by homogenizing an aqueous fluid having a cell density effective for crystallization of alcohol oxidase in a recovery range solution having a molar ionic strength in the range of between 0.05 M and about 0.01 M, against a dialysis medium across a membrane impermeable to the alcohol oxidase but permable to dialysis medium water and buffer molecules, if any, to achieve on enzyme side of the membrane the recovery range solution thereby resulting in crystalline alcohol oxidase, and separating the resulting crystalline alcohol oxidase from the dialysis medium. My invention also comprises the novel isolated alcohol oxidase. My invention further comprises using the novel alcohol oxidase to determine short chain alcohol concentration of selected samples.

DESCRIPTION OF THE PREFERRED EMBODIMENTS

FERMENTATION PROCESS

The alcohol oxidase of my invention is produced by species of Pichia-type yeasts which are yeasts of the genus Pichia and those which are genetically and/or taxonomically closely related to Pichia, preferably of the genus Pichia itself, and which are capable of utilizing a feedstock containing methanol as carbon and energy source.

Specific examples of such methanol utilizing Pichia yeasts include
*Pichia pastoris*
*Pichia pinus*
*Pichia trehalophila*
*Pichia molischiana*

Two exemplary strains of suitable yeasts of the species *Pichia pastoris* have been deposited with the United States Department of Agriculture, Agriculture Research Service, Northern Regional Research Laboratories of Peoria, Illinois, and have received the numerical designations NRRL Y-11430 and Y-11431.

According to the present invention, a selected species of methanol competent Pichia-type yeast is cultured under aerobic aqueous fermentation conditions using methanol as the carbon and energy source. Preferably the methanol is supplied under conditions so that methanol is the growth-limiting factor. The methanol limiting conditions are defined for purposes of my disclosure as a concentration of methanol which is the minimal concentration of methanol which results in a maximum growth rate for a given set of fermentation culture conditions. Preferably fermentation is conducted under high cell density conditions, i.e., so that the cell density is 100 grams or greater on a dry weight basis per liter of ferment. The selected yeast is grown in a batch or continuous process in the presence of oxygen, methanol, and an assimilable source of nitrogen. Various types of fermentation processes and apparatuses known in the art can be utilized. For example, a foam-type fermenter such as describer in U.S. Pat. No. 3,982,998, or other suitable fermenter can be used.

Oxygen can be supplied to the fermenter as such, or in the form of air or oxygen-enriched air, in a range of pressures from such as about 0.1 atm. to 100 atm., as is known in the art. The assimilable source of nitrogen for the fermentation can be any organic or inorganic nitrogen containing compound which provides nitrogen in a form suitable for metabolic utilization by the microorganisms. Suitable organic nitrogen sources include, for example, proteins, amino acids, urea, and the like. Suitable inorganic nitrogen sources include, for example, ammonia, ammonium hydroxide, ammonium nitrate, and the like. The presently preferred nitrogen sources includes ammonia and ammonium hydroxide for convenience and availability.

The pH range in the aqueous microbial ferment should be in the range of about 3 to 7, more preferably and usually about 3.5 to 5.5. Preferences of certain microorganisms for a pH range are dependent to some extent on the medium employed, as well as on the particular microorganisms, and thus may change somewhat with change in medium as can be readily determined by those skilled in the art.

Sufficient water is maintained in the fermentation means so as to provide for the particular requirements of the microorganisms employed as well as to provide a carrier fluid for water soluble nutrients. Minerals, growth factors, vitamins, and the like, generally are added in amounts which vary according to the strain of microorganisms utilized and the selected culture conditions, and are known to those skilled in the art or are readily determinable by them. A typical nutrient medium is set forth below in the introduction to the examples.

The growth of the microorganism is sensitive to the operating temperature of the fermenter and each particular strain of microorganism has an optimum temperature for growth. Exemplary fermentation temperatures are in the range of about 20° C. to about 65° C. The temperature selected will generally depend upon the microorganism employed in the process since each one will have a somewhat different temperature/growth rate relationship.

Fermentation pressures are generally within the range of about 0.1 to about 100 atmospheres, more usually about 1 to about 30 atmospheres, and more preferably about 1 to about 5 atmospheres since the higher pressures result in a greater level of dissolved oxygen in the aqueous medium and usually higher cell productivities.

ALCOHOL OXIDASE ISOLATION

In the isolation of my novel alcohol oxidase a fluid is prepared which is an aqueous suspension containing cells of the selected microorganism. The aqueous fluid can be fermenter effluent which can be used directly, or preferably after adjusting the pH as described below. Alternatively the suspended microorganism cells can be initially separated from the fermentation medium, for example, by centrifugation or by filtration through filters having a pore size less than the size of the individual cells, and subsequently resuspended in a convenient volume of water or of an appropriate aqueous buffer, for example $KH_2PO_4/Na_2HPO_4$ buffer at 0.2 M. It has been found that the cell density in the aqueous suspension must be greater than a minimum crystallization density. Satisfactory results are obtained if the fluid cell density is greater than about 75 grams on a dry weight basis per liter of fluids. It has been found that satisfactory results are obtained if the fermenter effluent, where it is to be used as the fluid, is first adjusted to a pH of such as about 7.5 by addition of a base such as ammonium hydroxide, sodium hydroxide, and the like. The pH is not considered critical, however and the pH of the aqueous suspension need not be adjusted prior to homogenization. However, it is considered preferable to adjust the pH broadly in the range of about 6–9 since in this range the enzyme is active and stable.

The cell-containing fluid is homogenized by suitable means known in the art. For example, fermenter effluent containing yeast grown on methanol can be adjusted to a pH of about 7.5 and homogenized at a high cell density concentration such as 100–120 grams biomass (dry weight)/liter use a Dynomill TM Model KDL using a 0.6 liter vessel in a continuous operation at 5° to 30° C. using belt combination #3 and a flow of 20–30 ml/hr. The homogenate solids are separated from the homogenate to produce a crude solution containing my novel alcohol oxidase as a soluble component. For example, the homogenate solids can be removed by centrifugation to yield a cell-free supernatant. Alternatively the solids can be removed by filtration through filters having a suitable pore size, followed by pH adjustment if desired. If desired, for further purification steps such as recovery of crystalline alcohol oxidase, the pH can be adjusted to have a pH in the range of 5.75 to 6.75 as desired, for example, to pH 6.5.

The crude solution containing my alcohol oxidase has effective enzymatic activity and finds useful application in that form. As such, it constitutes a part of my invention. However, the alcohol oxidase of my invention has specific properties as hereinafter set forth which are best realized by the isolation of the crystalline alcohol oxidase.

PREPARATION OF CRYSTALLINE ALCOHOL OXIDASE

The crude solution containing the soluble alcohol oxidase can be treated to recover my novel my alcohol oxidase either in more concentrated solid form by such as by fractional precipitation with ammonium sulfate, or most desirably and preferably as the potent crystalline form exhibiting highest activity by treatment under dialysis conditions either by conventional dialysis modes or by applying ultrafiltration to increase the rate of recovery.

In dialysis, the crude solution containing the soluble alcohol oxidase is dialyzed against a dialysis medium across a membrane impermeable to alcohol oxidase but permeable to water, buffer, and inorganic molecules. The crude solution is prepared by homogenizing an aqueous fluid having a cell density effective for crystallization of alcohol oxidase when the solution attains a recovery range solution condition as herein described. Satisfactory crystallization has been observed where the effective cell density is about 75 grams (on a dry weight basis) per liter of aqueous fluid. Crystallization is also expected to occur at even lower effective cell densities although the amount of crystalline alcohol oxidase recovered is less. Below an empirically determinable minimum cell density (minimum crystallization density) essentially no crystalline alcohol oxidase is recovered. The type of membrane used is not considered critical and any suitable membrane may be used. For example, commerically available cellulose acetate dialysis tubing can be used to form dialysis bags or otherwise used, or hollow fiber dialysis cells can be used. The alcohol oxidase containing solution is dialyzed against a dialysis medium, for example water or a buffer solution, to achieve a recovery range solution on the enzyme side of the membrane have an ionic strength in a recovery range of between 0.05 M and 0.01 M thereby effecting precipitation of an electrophoretically homogeneous crystalline oxidase.

The dialysis medium can be any medium whereby during dialysis the molar ionic strength of the solution on the enzyme side of the membrane passes through at least a portion of the recovery range. For example, if the crude solution containing alcohol oxidase has a molar ionic strength of 0.2 M, the dialysis medium can be a suitable volume of distilled water. The volume of fluid against which the enzyme is dialyzed is not considered critical so long as the ionic strength on the enzyme side of the membrane passes through at least a portion of the recovery range.

During dialysis, the pH of the alcohol oxidase containing solution should be maintained in the range of about 5.75 to about 6.75 by use of a suitable buffer system. A suitable buffer system comprises, for example, potassium dihydrogen phosphate and disodium hydrogen phosphate. Preferably the pH range is from about 6.0 to about 6.5 for recovery of maximum amounts of crystalline alcohol oxidase. As shown in the example below, good crystallization of the alcohol oxidase has been observed within the broad pH range, and the narrow range represents a presently preferred pH range to achieve minimum solubility of the enzyme.

The alcohol oxidase of my discovery has been found to have minimum solubility under these conditions in solutions of 0.02 M ionic strength at pH 6.0 to 6.25. Consequently, optimum crystallization is achieved by planning the dialysis to obtain these conditions. Good crystallization can be achieved by exhaustive dialysis of the enzyme containing solution against large volumes of buffers meeting the above conditions. Alternatively, the dialysis system can be designed to achieve optimal crystallization conditions either at equilibrium or at a point in time after the start of dialysis. For example, a crude enzyme solution having an ionic strength of 0.2 M at pH 6.25 can be dialyzed against a nine-fold excess of distilled water (relative to the volume of the crude enzyme solution). At equilibration, the ionic strength of the crude enzyme solution will be 0.02 M and crystallization will occur. Such a method has the disadvantage that a relatively long period of time is required for equilibration to occur.

On the other hand, if the crude enzyme solution has a molar ionic strength of, for example, 0.05 M, dialysis against a nine-fold excess of distilled water (relative to the volume of the crude enzyme solution) to equilibration will result in a solution having 0.005 M ionic strength and crytals formed will tend to redissolve since the equilibrium ionic strength is outside the recovery range. However, the crystals will form after a relatively shorter dialysis time and may then be removed and recovered before system equilibration and redissolution. This latter method of dialysis is presently preferred because of the decreased time required to recover crystalline alcohol oxidase.

The dialysis can be safely carried out at temperatures in the range of from about 4° C. to about 40° C. Sufficient time, generally more than one hour, and preferably 18 hours, or more, must be allowed for crystallization to occur.

At the end of dialysis, the alcohol oxidase is present in the dialysis bag as a crystalline solid. The crystalline alcohol oxidase can be readily separated from the dialysis medium, such as by decanting the liquid in the dialysis bag from the solid crystals. The moist crystals can be further processed as desired for storage. For example, the crystal slurry can be followed by lyophilization to form a dry powder, or can be dissolved in water or more preferably in a phosphate buffer. Stabilizer compounds known to stabilize enzyme solutions against denaturation and loss of enzymatic activity can be added, such as sucrose or glycerol. It is preferable to store the prepared enzyme at temperatures in the range of about 4° C. to about 40° C. More preferably, the enzyme is stored at temperatures in the range of about 4° C. to 24° C. Most preferable is storing the enzyme at about 4° C. Only minimal loss of activity has been found to occur when the enzyme is stored at 4° C. in 0.1 M phosphate buffer at pH 7.5, and with 0.02% sodium azide to inhibit microorganism growth. However, my alcohol oxidase can also be stored frozen without significant loss of enzymatic activity.

In the process of preparing alcohol oxidase from Pichia microorganisms according to my invention, a crystalline solid is formed during dialysis of the crude enzyme solution and no further purification steps have been found necessary. My novel crystalline alcohol oxidase is a readily prepared and relatively inexpensive alcohol oxidase available for applications otherwise economically unattractive.

CHARACTERIZATION OF PICHIA ALCOHOL OXIDASE

The alcohol oxidase isolated from Pichia-type microorganisms is typified by the alcohol oxidase isolated from *Pichia pastoris*. My "Pichia" alcohol oxidase is homogeneous as judged by sodium dodecyl sulfate (SDS) gel electrophoresis. Very little, if any, of the original catalase activity of the cells remains associated with my crystalline alcohol oxidase. My alcohol oxidase enzyme is estimated to comprise 6 or more subunits, of an estimated molecular weight of 72,000 per subunit as estimated by SDS gel electrophoresis and a rough estimate of the molecular weight of the alcohol oxidase. My enzyme is a flavoprotein having FAD (flavin adenine dinucleotide) as a coenzyme comprising about one FAD moiety per enzyme subunit. The apparent Michaelis constant, $K_m$, for methanol is about 0.7 mM. Electrophoretic analysis suggests that the molecular weight of my Pichia enzyme is larger than that of an alcohol oxidase isolated from *Candida boidinii*. My Pichia enzyme differs from an alcohol oxidase isolated from *Hansenula polymorpha* in the extent to which it binds sodium azide, and in its ability to form crystals in 0.02 M sodium phosphate at pH 6.5.

Characteristics of the Pichia enzyme having been determined and are shown in Table I. Reactivities toward various substrates are shown normalized with reference to methanol which is set equal to 100%.

TABLE I

| Characteristic | Pichia pastoris |
|---|---|
| Molecular wt. | 500,000 (est.) |
| Coenzyme | FAD |
| No. of subunits | 6 or more (est.) |
| Optimal Activity Temperature (°C.) | |
| (broadly) | 35°–45°+ |
| (optimum) | 45° |
| pH | |
| (broadly) | 6–9 |
| (optimum) | 8.0 |
| Km for methanol (mM) | 0.7 |
| Inhibitors | HCHO >30 mM |

My Pichia alcohol oxidase differs from other other reported alcohol oxidases in a number of ways. In particular, the alcohol oxidase from *Pichia pastoris* is reactive toward the lower alcohols and formaldehyde, but is not reactive toward acetaldehyde or organic acids. This lack of reactivity toward acetaldehyde and organic acids is of distinct benefit, for example in use of my Pichia-derived alcohol oxidase in procedures for determining alcohol concentration in organic fluids such as blood because interference due to the presence of aldehydes and organic acid materials is avoided.

ALCOHOL OXIDASE ELECTRODE

The alcohol oxidase of my invention catalyzes the following reaction $$RCH_2OH + O_2 \rightarrow RCHO + H_2O_2$$

where R is hydrogen or lower alkyl, generally selected from the group consisting of H—, $CH_3$—, $CH_3CH_2$—, and $CH_3(CH_2)_2$—. Accordingly, my enzyme can be used for the production of aldehydes and hydrogen peroxide as well as for the removal of oxygen from enzyme compatible fluids where the presence of oxygen is undesirable.

Furthermore, since in the course of the reaction oxygen is consumed and aldehydes and hydrogen peroxide are produced, my enzyme can be used to determine the concentrations of short chain alcohols $RCH_2OH$ in a fluid sample under conditions compatible with enzymatic activity. For example, my enzyme can be used to determine the concentration of lower alcohols in biological fluids such as the concentration of methanol in a fermentation process or the concentration of ethanol in body fluids such as blood.

A particularly convenient way of determining such alcohol concentrations is to immobilize the alcohol oxidase on the tip of a polarographic dissolved oxygen electrode. Several such polarographic dissolved oxygen electrodes are commercially available and are suitable for utilization with my alcohol oxidase enzyme. For example, a Clark or a Beckman dissolved oxygen electrode can be used.

The alcohol oxidase can be immobilized on the electrode tip by any suitable method. For example, the enzyme can be blended with suitable supporting materials to form a paste which is held as a thin film on the electrode tip by a membrane permeable to the compound whose concentration is to be determined, but impermeable to the enzyme itself. For example, the supporting material may be DEAE Sephadex, a polysaccharide ion exchange resin from Pharmacia Fine Chemicals, Sweden. For ethanol determinations, a suitable membrane is cellulose acetate film through which film ethanol has a satisfactory mobility. Of course, the enzyme can also be covalently bonded to an appropriate electrode membrane or can be physically incorporated in an appropriate polymer film.

Conditions compatible with ezymatic activity includes a fluid sample pH in the range of about pH 6 to about pH 9 and preferably about pH 8.0 for maximum sensitivity, and a fluid sample temperature in the range of about 25° C. up to and including 45° C. and preferably at about 25° C. for convenience. The sample pH can be adjusted with ammonium hydroxide solutions or dilute hydrochloric acid solutions as required.

Preferably, a calibration curve is prepared using a series of known concentrations of the compound to be assayed and the concentration of the compound in the fluid sample is determined therefrom as is known in the art.

To determine the alcohol concentration, the sample electrode is immersed in an aliquot of the thus prepared fluid to be examined. The substrate alcohol diffuses across the membrane and in the presence of oxygen reacts to produce an aldehyde product and hydrogen peroxide. The reaction is followed by observing the rate of change of oxygen concentration in the sample. Since the catalyzed reaction is stoichiometric, the concentration of the alcohol $RCH_2OH$ can be determined from the rate of change in oxygen concentration as is known in the art. Alternatively, the reaction can be followed polarographically with reference to the hydrogen peroxide produced. In yet another application, the reaction can be followed galvimetrically.

The use of my alcohol oxidase for the determination of alcohol concentration in biological fluids, for example, determination of ethanol concentration in a blood sample or short chain alcohol concentration in fermenter broths, is particularly advantageous in view of the relatively low reactivity of the instant oxidase to aldehydes and organic acids and is thus not so subject to interference by such compounds which may be present in biological fluids such as blood.

To further illustrate the instant invention, the following examples are provided.

EXAMPLES

The following fermentation is typical of the several fermentations carried out to provide the effluent for isolation of the alcohol oxidase.

In a continuous aerobic fermentation process, methanol and an aqueous mineral salts medium in a volume ratio of about 40 to 60, respectively, were fed individually to a fermenter, innoculated with the yeast species *Pichia pastoris* NRRL Y-11430, at a rate so that methanol is the growth-limiting factor. The fermenter was a 1500-liter foam-filled fermenter with a liquid volume of about 610 liters, with automatic pH, temperature, and level control. Agitation was provided by two conventional paddle-type turbines driven at 1000 rpm. The aeration rate was about 4 volumes of air (at about 38 psig and about 25° C.) per volume of ferment in the fermenter per minute. Anhydrous ammonia was added at such a rate as to maintain the pH of the fermentation mixture at about 3.5.

The aqueous mineral salts medium was prepared by mixing, with each liter of tap water, 15.86 ml 75 percent $H_3PO_4$, 9.53 g $K_2SO_4$, 7.8 g $MgSO_4.7H_2O$, 0.6 g $CaCl_2.2H_2O$, and 2.6 g 85 percent KOH. The trace mineral solution plus biotin was fed separately via the methanol stream at a rate of 10 ml per liter of methanol. The trace mineral solution plus biotin was prepared by mixing 780 ml of a trace mineral solution, 20 ml water, 200 ml methanol and 0.032 g biotin.

The trace mineral solution was prepared by mixing, for each liter of solution, 65 g $FeSO_4.7H_2O$, 20 g $ZnSO_4.7H_2O$, 3.0 g $MnSO_4.H_2O$, 6.0 g $CuSO_4.5H_2O$, 5.0 ml conc. $H_2SO_4$, and sufficient deionized water to make 1 liter of solution.

The aqueous mineral salts medium was fed at a rate of 31.5 liters per hour and the methanol at a rate of 21 liters per hour.

The fermentation was conducted at about 30° C. and about 38 psig pressure, with a retention time of 11.6 hours.

For analytical purposes, the resulting yeast cells were separated from the fermentation effluent (ferment) by centrifugation, washed by suspension in water and recentrifugation, dried overnight at 100° C., and weighed. On a dried basis, the yield of yeast cells typically was about 40.6 g per 100 g of methanol fed. The cell density typically was about 128.4 g of cells per liter of fermenter effluent. The total solids content of the ferment typically was about 134.7 g per liter, cells plus dissolved solids. A portion of the fermenter effluent was frozen and stored.

In Examples I, IX, and X, the alcohol oxidase activity for reaction with methanol was determined by the following assay procedure (Procedure A). A dye-buffer mixture was prepared by mixing 0.1 ml of an o-dianisidine solution (1 weight % o-dianisidine in water) with 12 ml of aerated 0.1 M sodium phosphate buffer (pH 7.5). The assay mixture was prepared with 2.5 ml of the dye-buffer mixture, 50 μl of methanol, 10 μl of a peroxidase solution (1 mg of horse-radish peroxidase-Sigma, Type II), and 25 μl of the alcohol oxidase solution. The assay mixture was maintained at 25° C. in a 4×1×1 cm cuvette and the increase in absorbance by the dye at 460 nm was recorded for 2 to 4 minutes. The enzyme activity was calculated by $$\text{Activity } (\mu \text{ mole/min/ml}) = \frac{\Delta A}{\text{min}} \times 11.5$$

wherein 11.5 is a factor based on a standard curve prepared with known aliquots of $H_2O_2$ and $\Delta A$ is the change in absorbance during the experimental interval.

In Examples III and IV another assay procedure (Procedure B) was used. A MBTH stock solution was prepared with 0.04 g of MBTH (3-methyl-2-benzothiazoline hydrazone, available from Sigma Chemical Company, St. Louis, Missouri) per 100 ml of a 0.05 M phosphate buffer (pH 7.5). A ferric chloride stock solution was prepared from 0.2 g of ferric chloride per 100 ml of 0.1 N HCl. A 1 ml portion of the MBTH solution was added to 25 μl of the alcohol and they were mixed. A 25 μl solution of the alcohol oxidase solution was added and the mixture was incubated for 10 minutes at 25° C. A 4 ml sample of the ferric chloride solution was added to the mixture and the resulting mixture was allowed to stand for 1 hour at the desired temperature. The dye absorbance at 625 nm was recorded on a colorimeter using a 1 cm path length cuvette. The sample activity is reported at the absorbance peak height.

EXAMPLE I

Fermentation of *Pichia pastoris* NRRL Y-11430 was carried out by a method of which that set forth above is typical. A portion of the fermenter effluent was removed and adjusted to pH 7.5 with ammonium hydroxide, and was homogized on a Dyno-Mill Model KDL using a 0.6 liter vessel in a continuous operation at 30° C. using belt combination #3 and a flow of 20–30 ml/hr. The beads in the mill were lead free glass beads with a diameter of 0.3–0.5 mm. The resulting homogenate was centrifuged at 5° C. and 20,000×g for 30 minutes to yield a cell-free supernatant. The cell-free supernatant enzyme activity (using Procedure A) was about 330 U/ml. The supernatant was stored frozen for future use.

Six 130 ml portions of the supernatant were placed in cellulose acetate dialysis bags and dialyzed at 5° C. against about 8 liters of distilled water. After 4 days, the aqueous phase of each bag was decanted. The solids remaining in the bags consisted of two types of solid. The thin upper white layer was carefully removed and discarded. The bottom solid was brown-yellow and was the alcohol oxidase. A portion of the alcohol oxidase was dissolved in distilled water (about 10 times the volume of the solid) and an assay by Procedure A showed an activity of 94 U/ml. The specific activity of the alcohol oxidase was 10.4 U/mg of protein.

A sample of the solid alcohol oxidase was examined by SDS gel electrophoresis and a single band was observed indicating a homogeneously pure enzyme. A comparison of electrophoretic mobility with those of proteins having known molecular weight indicates a subunit molecular weight of about 72,000.

The results of this example demonstrate the process of my invention for the preparation and isolation of pure crystalline alcohol oxidase from *Pichia pastoris*.

EXAMPLE II

A portion of frozen supernatant that had been prepared as described in Example I was thawed and centrifuged to clarify the solution. Six dialysis bags containing 1 ml of the clarified supernatant were each extensively dialyzed overnight against 500 ml of aqueous solutions containing a phosphate buffer of differing ionic strengths (all at pH 7.5). In dialyses 1, 2 and 3 at 0.5 M, 0.1 M and 0.05 M phosphate respectively, no precipitate was obsrved. The maximum amount of precipitate was observed in dialysis 4 at 0.02 M phosphate. dialyses 5 and 6 at 0.01 and 0.005 M phosphate, respectively, contained less precipitate than in dialysis 4. However, in dialyses 5 and 6, some of the precipitate formed earlier had redissolved.

The results of these runs demonstrate that precipitation of my alcohol oxidase during dialysis occurs at phosphate buffer levels below about 0.05 M. The alcohol oxidase appears to be least soluble at 0.02 M phosphate. At buffer levels of about 0.01 M and below, dialysis beyond the time required for maximum precipitation can result in redissolving of the crystalline solids.

EXAMPLE III

A series of assays using assay Procedure B was carried out using different pH values to determine the relative activities of my alcohol oxidase (as the cell-free supernatant from a homogenation) at various levels of pH. The pH of each assay solution was varied by the addition of HCl or NaOH. The relative activity at each pH is expressed as an absorbance at 625 nm.

| pH of Solution | Absorbance At 625 nm |
|---|---|
| 4.1 | 0.06 |
| 5.1 | 0.19 |
| 6.1 | 0.33 |
| 7.1 | 0.38 |
| 8.1 | 0.41 |
| 9.1 | 0.33 |
| 10.3 | 0.09 |

These results indicate that the pH optimum is about pH 8 and a working range is about 6 to about 9.

EXAMPLE IV

Another series of assays using assay Procedure B was carried out using different assay temperatures to determine the influence of assay temperature on relative activity. Samples of alcohol oxidase from *Pichia pastoris* were dissolved in 0.05 M phosphate buffer (pH 7.5). The samples were assayed at various assay temperatures and the relative activities are expressed as an absorbance at 625 nm.

| Assay Temperature, °C. | Absorbance At 625 nm |
|---|---|
| 27 | 0.42 |
| 36 | 0.54 |
| 45 | 0.60 |
| 55 | 0.27 |
| 65 | 0.05 |

These results demonstrate that the temperature optimum for the alcohol oxidase activity from *Pichia pastoris* is about 45° C. and the working range is about 35° C. to 45° C. inclusive.

EXAMPLE V

In a control run, the alcohol oxidase from *Hansenula polymorpha* was dialyzed according to the method of my invention to demonstrate that an alcohol oxidase from a yeast genus other than Pichia did not form a pure, crystalline solid as does my invention. A continuous aerobic aqueous fermentation was carried out in which a yeast species *Hansenula polymorpha* (NRRL Y-11170) was grown on methanol under aqueous fermentation conditions. A portion of the fermenter effluent was homogenized and centrifuged as described in Example I. The cell-free supernatant was dialyzed at 0° C. against a 0.005 M phosphate buffer in a series of dialyses using pH values from 5.5 to 7.75 at 0.25 pH intervals. In each dialysis no precipitate formed in the dialysis bag after 20 hours.

In a series of comparison dialyses carried out at the same time with the alcohol oxidase derived from *Pichia pastoris* NRRL Y-11430, precipitation of the crystalline alcohol oxidase occurred at pH values between about 5.75 and about 6.75. The largest amounts of precipitate were formed at pH 6.0 and 6.25.

The results of these runs show that the alcohol oxidase from *Hansenula polymorpha* does not crystallize during dialysis under conditions effective for the crystallization of the alcohol oxidase of *Pichia pastoris*. This difference in crystalization behavior is notable. It demonstrates a significant advantage for my alcohol oxidase obtained from the *Pichia pastoris* because of the rapid and inexpensive method of recovery of pure crystalline enzyme.

EXAMPLE VI

The alcohol oxidase isolated from *Pichia pastoris* was immobilized on the tip of a dissolved oxygen electrode for use in the determination of the amount of ethanol in samples. The solid alcohol oxidase and DEAE Sephadex (in a weight ratio of about 1:1) were mixed and applied to the Teflon membrane on the tip of a Beckman dissolved oxygen probe. A cellulose acetate dialysis membrane was used to hold the alcohol oxidase-DEAE Sephadex mixture to the electrode tip. The electrode was attached to an analog differentiator which gave the analysis results as a peak height which is proportional to the alcohol concentration in the sample. The electrode was calibrated with a series of standard ethanol solutions. In each case, the sample was added to the electrode chamber which contained a 3.3 ml of 0.05 M phosphate buffer (pH 7.5) at 25° C. The calibration curve of peak height vs. alcohol concentration was linear up to a final concentration at the tip of the alcohol oxidase electrode of about 0.1 volume % alcohol (1000 ppm). The alcohol oxidase electrode as constructed worked effectively for alcohol determinations for at least one month. The electrode exhibited rapid response (assay time of about 15 seconds) and was sensitive to concentrations of ethanol as low as 0.2 ppm by volume.

EXAMPLE VII

The alcohol oxidase electrode described in Example VI was used to determine the relative reactivity of the alcohol oxidase towards various substrates. In each determination, a 1 to 10 μl solution of the substrate in water (1 volume %) was added to the 3.3 ml phosphate buffer (pH 7.5) in the electrode chamber and the peak height was recorded. The results are listed below with the relative reactivities corrected for sample size and normalized with methanol set equal to 100.

|  | Relative Reactivity |
|---|---|
| Methanol | 100 |
| Ethanol | 27 |
| 1-Propanol | 10 |
| 1-Butanol | 5 |
| Formaldehyde | 30 |

2-Propanol, 2-methyl-1-propanol, 1-pentanol, acetaldehyde, and ethylene glycol had relative activities less than one. Sodium formate, sodium acetate, cyclohexanol, and 1,4-butanediol were essentially inactive.

The results of this example show that the alcohol oxidase electrode of this invention is highly specific for short chain alcohols and formaldehyde. The differences in reactivities of the enzyme observed in this example and those observed in Example XII are believed due in part to different mobilities of the substrate molecules across the cellulose acetate membrane employed in this run. The differences may also be due in part to differences in purity of the prepared alcohol oxidase.

EXAMPLE VIII

A series of samples of human blood serum were mixed with known quantities of absolute ethanol, and a series of samples of 0.05 M phosphate buffer were also mixed with known quantities of absolute ethanol. In both series, the ethanol levels were 0, 0.01, 0.02, 0.05, and 0.10 volume % ethanol. 50 μl samples from each solution were assayed using the alcohol oxidase electrode described in Example VI.

Plots of peak heights vs. ethanol levels gave linear and nearly identical plots for both series of samples. These results show that other components, for example, aldehydes and organic acids, in blood serum do not interfere with alcohol concentration determination using an alcohol-sensing electrode containing the alcohol oxidase from a Pichia-type microorganism.

EXAMPLE IX

A series of samples containing alcohol oxidase isolated as the pure crystalline solid by dialysis from *Pichia pastoris* NRRL Y-11430 were held at 40° C. for up to two weeks to determine thermal stability. The alcohol oxidase was added to a 0.5 M phosphate buffer (pH 7.5) at a concentration of 2.2 mg protein/ml. Another sample of alcohol oxidase was dissolved in 50 volume % aqueous glycerol. Another sample of alcohol oxidase was lyophilized. The three samples were assayed by Procedure A at intervals during the two-week test. The result are summarized below.

| Alcohol Oxidase | Orignial Enzyme Activity, U/ml | Enzyme Activity, U/ml | | |
|---|---|---|---|---|
| | | 2 Days | 1 Week | 2 Weeks |
| Buffer | 31 | 34 | 31 | 30.5 |
| 50% Glycerol | 29 | 51 | 30 | 18 |
| Dry Solid[a] | 13 | 6 | 3.5 | 2 |

[a] The solid was dissolved in a 0.05 M phosphate buffer (1 mg protein/ml) for each assay.

The results of these runs show that the activity of my alcohol oxidase in the buffer solution was essentially unchanged after two weeks at 40° C. The activity of the alcohol oxidase in 50% glycerol was unchanged after one week, but had lost some of its activity after two weeks at 40° C. The freeze dried solid lost most of its activity during the thermal test. However, the lyophilized alcohol oxidase had excellent stability at 4° C.

EXAMPLE X

A study was made to determine the stability of the alcohol oxidase derived from a *Pichia pastoris* in solution at several temperatures. The fermenter effluent from the aerobic fermentation of *Pichia pastoris* NRRL Y-11430 was homogenized and centrifuged as described in Example I. The cell-free supernatant was fractionally precipitated with ammonium sulfate. The resulting enzyme was estimated from its enzymatic activity to be less than 50% pure.

The thus partially purified alcohol oxidase (0.1 ml) was added to 10 ml samples of distilled water containing 0.02 weight % sodium azide (hereinafter referred to as sodium azide solution) and to 10 ml samples of 0.1 M phosphate buffer (pH 7.5) containing 0.02 weight % sodium azide (hereinafter referred to as sodium azide-buffer solution). The solutions were held at 4°, 24°, 30°, or 40° C. for one month with intervallic assays of aliquots for activity using Procedure A. The sodium azide and sodium azide-buffer solutions held at 4° C. showed no loss in activity during the test period. The sodium azide and sodium azidebuffer olutions held at 24° C. were estimated by extrapolation of test data to lose about half of their activity (half-life) in 40 days. At 30° C., the sodium azide-buffer solution has a half-life of about 30 days while the sodium azide solution had a half-life of about 10 days. At 40° C. the sodium azide-buffer solution had a half-life of about 15 days, while the sodium azide solution had a half-life of only about 3 days.

EXAMPLE XI

A sample of frozen cell-free supernatant obtained from *Pichia pastoris* NRRL Y-11430 by homogenization and centrifugation as described in Example I was cleared by centrifugation and adjusted to pH 6.5 with hydrochloric acid. The supernatant then was dialyzed for 5.5 hours against distilled water (supernatant/water volume ratio of 1/10). The resulting solid crystalline alcohol oxidase was recovered by decanting the dialysis supernatant from the solid enzyme. The catalase activity, using the method of R. F. Beers and I. W. Sizer, J. Biol. Chem., 195, 133 (1952), of the starting cell-free supernatant was 6973 U/ml while the catalase activity of the dialysis supernatant was 6697 U/ml. Therefore, over 90% of the initial catalase activity in the cell-free supernatant remains in the dialysis supernatant after conclusion of the dialysis.

EXAMPLE XII

The reactivity of the alcohol oxidase from *Pichia pastoris* towards various substrates was determined using the previously described assay Procedure A. The fermentation effluent from the aerobic fermentation of *Pichia pastoris* NRRL Y-11430 in a manner similar to the fermentation described before Example I was homogenized and centrifuted. The cell-free supernatant was fractionally precipitated with ammonium sulfate to yield a partially purified alcohol oxidase. Assay Procedure A was used with the appropriate substrate being substituted for methanol.

The results in terms of relative reactivity normalized with methanol set equal to 100 are listed below.

| Substrate | Relative Reactivity |
|---|---|
| Methanol | 100 |
| Ethanol | 100 |
| 1-Propanol | 73 |
| 2-Propanol | 4 |
| 1-Butanol | 45 |
| 2-Methyl-1-propanol | 9 |
| 1-Pentanol | 5 |

These result indicate that this partially purified alcohol oxidase from *Pichia pastoris* is reactive towards the lower, straight chain, primary alcohols.

EXAMPLE XIII

A run was carried out to determine the influence of the enzyme concentration on the formation of pure, crystalline alcohol oxidase during dialysis according to the alcohol oxidase purification procedure of the present invention. An aerobic fermentation of *Pichia pastoris* NRRL Y-11430 was carried out at a cell density of about 150 g (dry weight) per liter. The fermenter effluent was homogenized and centrifuged to yield a cell-free supernatant. A series of samples was prepared from the cell-free supernatant by a series of dilutions with water. Five of the samples (2 ml each) were dialyzed against 100 ml of 0.01 M phosphate buffer (pH 6.5) for 4–5 hours. Sample 6 was a duplicate of sample 5 and was not dialyzed. At the conclusion of the dialyses, the liquids in the 5 dialysis bags and the undialyzed sample were assayed for enzyme activity by assay Procedure A. Where precipitates were formed during the dialysis, the solid was isolated by decanting the liquid and was dissolved in 2 ml of a phosphate buffer for assay by Procedure A. The results are presented below.

| Sample | Dilution | Effective Cell Density$^{(a)}$, g/l | Activity Before Dialysis$^{(b)}$, U/ml | Activity of Supernatant$^{(c)}$, U/ml | Activity of Precipitate$^{(d)}$, U/ml |
|---|---|---|---|---|---|
| 1 | Undiluted | 150 | 200 | 35.5 | 165.6 |
| 2 | 2 × | 75 | 100 | 56.8 | 45.1 |
| 3 | 4 × | 37.5 | 50 | 53.3 | $(e)$ |
| 4 | 8 × | 18.75 | 25 | 25.9 | $(e)$ |
| 5 | 16 × | 9.4 | 11 | 11.3 | $(e)$ |
| 6 | 16 ×$^{(f)}$ | 9.4 | 10.1 | — | — |

$^{(a)}$Cell density of the fermenter effluent represented by the diluted sample in g (dry weight)/l of broth.
$^{(b)}$Estimated activity before dialysis is calculated from the activity of sample 5 after dialysis assuming no change in activity during dialysis and from the activity of undialyzed sample 6.
$^{(c)}$Activity of liquid in dialysis bag after dialysis.
$^{(d)}$Determined by dissolving solid precipitate in 2 ml of 0.5 M phosphate buffer (pH 7.5) for the assay.
$^{(e)}$No precipitate formed during dialysis.
$^{(f)}$This sample was not dialyzed.

Precipitates were formed during the dialysis of samples 1 and 2 which were the undiluted supernatant (150 g-dry/l cell density) and a two-fold dilution (representing an effective cell density of about 75 g-dry/l cell density) respectively. Precipitates were not formed in samples at the higher dilutions, which represent fermenter effluents from fermentations at effective cell densities of about 37.5 g (dry weight)/liter of broth and below. This suggests that fermenter effluents from fermentations at cell densities below about 40 g (dry weight)/liter of broth are not suitable for crystalline alcohol oxidase recovery. However, the fermenter effluents from such lower cell density fermentations can be concentrated using techniques such as ultrafiltrations, salt or solvent precipitation, and the like to provide materials suitable for the isolation of alcohol oxidase by my dialysis process.

Detailed embodiments and examples of the instant invention are disclosed herein. However, it is to be undertood that the disclosed embodiments and examples are merely exemplary of my invention which may be embodied in various forms. Therefore specific structural and functional details as disclosed herein are not to be interpreted as limiting but merely as a basis for the claims and as a representative basis for teaching one skilled in the art to variously employ the instatnt invention in any appropriate embodiment.

What is claimed is:

1. A method comprising:
   preparing an aqueous fluid containing a suspension of cells of a methanol utilizing microorganism of genus Pichia, said aqueous fluid having a cell density effective for crystallization of alcohol oxidase in a recovery range solution under suitable conditions of pH and ionic strength;
   homogenizing said fluid containing a suspension of cells to produce a homogenate; and
   removing suspended solids from the homogenate, thereby producing a solution containing soluble alcohol oxidase.

2. A method comprising:
   dialyzing a solution as prepared in claim 1 across a membrane impermeable to the alcohol oxidase but permeable to water and buffer molecules, if any, against a dialysis medium to achieve a recovery range solution, having a molar ionic strength in the range of about 0.05 M to 0.01 M and a pH of about 5.75 to 6.75, on any enzyme side of said membrane thereby resulting in crystalline alcohol oxidase; and
   separating the thus produced crystalline alcohol oxidase from the dialysis medium.

3. A method as in claim 2 employing a methanol-utilizing microorganism of genus Pichia cultured under methanol-limiting conditions.

4. A method as in claim 2 wherein:
   the methanol-utilizing microorganism of genus Pichia is selected from the group consisting of *Pichia pastoris*, *Pichia pinus*, *Pichia trehalophila*, and *Pichia molischiana*.

5. A method as in claim 2 wherein:
   the methanol-utilizing Pichia-type microorganism of genus Pichia is a strain of *Pichia pastoris* selected from the group consisting of *Pichia pastoris* NRRL Y-11430 and *Pichia pastoris* NRRL Y-11431.

6. A method as in claim 2 further comprising:
   culturing a methanol-utilizing microorganism of genus Pichia under aqueous aerobic fermentation conditions using methanol as a carbon and energy source to produce a ferment containing cells.

7. A method as in claim 6 wherein:
   a portion of said ferment is employed as said fluid containing a suspension of cells.

8. A method as in claim 6 further comprising:
   separating said cells from said fermenter effluent by centrifugation and resuspending in an aqueous medium to form said fluid containing a suspension of cells.

9. A method as in claim 6 further comprising:
   separating said cells from said fermenter effluent by filtration and resuspending in an aqueous medium to form said fluid containing a suspension of cells.

10. A method as in claim 7 wherein:
    said cells have a density in said fluid containing cells of greater than 75 grams on a dry weight basis per liter of fluid.

11. A method as in claim 7 further comprising:
    removing suspended solids from the homogenate by centrifugation.

12. A method as in claim 7 wherein:
    said recovery range solution is achieved at equilibration.

13. A method as in claim 12 wherein:
    said recovery range solution has a molar ionic strength of 0.02 M.

14. A method as in claim 7 wherein:
    said recovery range solution is achieved prior to equilibration.

15. A method as in claim 14 further
    separating a thus produced crystalline alcohol oxidase from the dialysis medium when said recovery range solution is about 0.02 M ionic strength.

16. A method as in claim 7 further
    separating the thus produced crystalline alcohol oxidase from the dialysis medium as a moist slurry followed by lyophilization.

* * * * *